United States Patent [19]

Stewart et al.

[11] Patent Number: 4,579,841

[45] Date of Patent: Apr. 1, 1986

[54] DIPEPTIDE DERIVATIVES HAVING OPIATE ACTIVITY

[75] Inventors: John M. Stewart; Raymond J. Vavrek, both of Denver, Colo.

[73] Assignee: University Patents, Inc., Westport, Conn.

[21] Appl. No.: 284,888

[22] Filed: Jul. 20, 1981

[51] Int. Cl.$^4$ .................. A61K 37/24; C07K 7/12
[52] U.S. Cl. ..................... 514/19; 514/809; 260/112.5 E
[58] Field of Search ............ 260/112.5 E; 514/809, 514/19

[56] References Cited

U.S. PATENT DOCUMENTS 4,127,535 11/1978 Coy et al. ............... 260/112.5 E
4,261,883 4/1981 Smolarsky ............... 260/112.5 E

OTHER PUBLICATIONS

Peptides 2(3) 305–307 (1981).
Peptide Chemistry (1981) 65–68.

*Primary Examiner*—Delbert R. Phillips
*Attorney, Agent, or Firm*—George M. Yahwak

[57] ABSTRACT

A class of dipeptide derivatives having opiate activity having the formula

Tyrosyl—X—Y wherein X is a D- or L-amino acid radical and Y is an amide or substituted amide are disclosed.

4 Claims, No Drawings

DIPEPTIDE DERIVATIVES HAVING OPIATE ACTIVITY

BRIEF SUMMARY OF THE INVENTION

This invention relates to dipeptide derivatives having opiate activity. Several classes of peptides having opiate activity have been described. Methionine-enkephalin and leucine-enkephalin (Hughes, et al., Nature 258:577-579, 1975) are well known, as well as numerous synthetic modifications of these structures (Morley, Ann. Rev. Pharmacol. 20:81-110. 1980); some of the latter modifications have high opiate potency. Recently a group of tetrapeptides was disclosed (Stewart, et al., U.S. Pat. No. 4,254,024; 1981) which also have high opiate potency. Although it has been stated that tetrapeptides are the minimum structures which could have significant opiate potency (Morley, reference above; Gorin et al., J. Med. Chem. 23:1113-1122, 1980), we have discovered that certain derivatives of dipeptides have high opiate potency. For example, Tyr-D-Ala-NH-$(CH_2)_3$-$C_6H_5$ produces a higher degree of analgesia in the mouse than does Tyr-D-Ala-Gly-Phe-Met-amide.

DETAILED DESCRIPTION OF THE INVENTION

The compounds of this invention are dipeptide derivatives having the structure

Tyrosyl-X-Y     (I)

wherein
X is a D- or L-amino acid radical
Y is an amide or substituted amide from the group —$NH_2$, —NH-R, or —$NR_1R_2$, where R may be —H, —alkyl or —aralkyl. The preferred dipeptide derivatives are those of formula I wherein
X is D-alanine or D-phenylalanine, and
Y is -NH-R-Ar, wherein R is an acyclic aliphatic group having from 1 to 4 carbon atoms or a substituted derivative thereof, and Ar is phenyl, substituted phenyl, condensed aromatic or substituted condensed aromatic.

The abbreviations used herein are those common to peptide chemistry and organic medicinal chemistry, and are understood by those skilled in the art. All amino acids are of the L-configuration unless stated otherwise.

The dipeptide derivatives may be synthesized by either solid phase or classical solution methods of peptide synthesis. These methods are described in Gross and Meienhofer, "The Peptides", Vol. 2, Academic Press, New York, 1980, and are well known in the art. Typical synthetic routes are described below.

The dipeptide derivatives of this invention are useful by virtue of their narcotic agonist activity. Such agonists find use as analgesics, anti-depressants, antipsychotics, antitussives and antidiarrheal agents. The compounds of formula I may be combined with various typical pharmaceutical carriers to provide compositions suitable for use in these applications. The dosage of these compounds depends upon various factors, such as the particular compound used and the response desired.

EXAMPLE 1

Synthesis of Tyr-D-Ala-phenylpropylamide

Boc-D-alanine was esterified to hydroxymethyl Merrifield peptide synthesis resin (hydroxymethyl poly(styrene-1% divinylbenzene)) by the use of dicyclohexylcarbodiimide and dimethylaminopyridine. The substitution of Boc-D-Ala on the resin was 0.25 mmoles/gram. Remaining hydroxyl groups were blocked by benzoylation with benzoyl chloride and triethyl amine. N-Boc-O-bromobenzyloxycarbonyl tyrosine was coupled to the D-Ala resin using a Beckman model 990 automatic peptide synthesizer, using standard procedures (Stewart and Young, "Solid Phase Peptide Synthesis", Freeman, San Francisco, 1969). The blocked dipeptide resin was shaken for 48 hr with 3-phenyl-n-propyl amine in methanol, and the blocked dipeptide phenylpropylamide was treated with anhydrous HF containing anisole at 0 degrees C. for 30 min to remove blocking groups. The resulting dipeptide amide was purified by countercurrent distribution for 100 transfers in the system n-butanol-acetic acid-water (4:1:5). The pure product was collected by evaporation of the solvent and lyophilization. It was homogeneous by high voltage electrophoresis and amino acid analysis.

EXAMPLE 2

Synthesis of Tyr-D-Phe-phenylpropylamide

Boc D-phenylalanine was esterified to hydroxymethyl resin as described in example 1 for Boc-D-alanine. The remainder of the synthesis, coupling of the tyrosine derivative, aminolysis of the peptide-resin and deprotection with HF and purification were as described in Example 1.

EXAMPLE 3

Synthesis of Tyr-D-Ala-3-indolylethyl amide

Boc-Tyr-D-Ala blocked dipeptide-resin was synthesized as in Example 1. The peptide was aminolyzed from the resin by treatment with tryptamine in the presence of a catalytic amount of triethyl amine; otherwise the synthesis and purification followed the procedures of Example 1.

EXAMPLE 4

Synthesis of Tyr-D-Phe-n-butylamide

Boc-Tyr-D-Phe protected dipeptide resin was synthesized as in Example 2, and the n-butyl amide was formed in a similar fashion by aminolysis with n-butyl amine. The dipeptide amide was deblocked and purified as above.

EXAMPLE 5

Synthesis of Tyr-D-Phe-isobutylamide

Boc Tyr-D-Phe protected dipeptide-resin was synthesized as in Example 2, and the isobutylamide was formed by aminolysis of the peptide from the resin with isobutyl amine. The peptide amide was deblocked and purified as described above.

Bioassay of peptides

Peptides were assayed for biological activity in vitro on the electrically stimulated guinea pig ileum, using the procedure described by Chipkin, et al. (Life Sciences 28:1517-1522, 1981). All potencies of the peptides in this assay are reported relative to the potency of methionine-enkephalin=100. Analgesic activity of the peptides in vivo was assayed by the tail-flick method following intracerebroventricular injection, as described in the Chipkin, et al., reference. The standard for this assay was Tyr-D-Ala-Gly-Phe-Met-amide.

Using these methods for the synthesis and bioassay of the peptides, the following peptides have been synthesized:

| Peptide | | Relate In Vitro Potency* |
|---|---|---|
| Tyr—Gly—Gly—Phe—Met | (Methionine-enkephalin) | 100* |
| Tyr—D-Ala—NH—$CH_2$—$C_6H_5$ | (benzylamide) | 8 |
| Tyr—D-Ala—NH—$CH_2CH_2$—$C_6H_5$ | (phenethylamide) | 6 |
| Tyr—D-Ala—NH—$CH_2CH_2CH_2$—$C_6H_5$ | (phenylpropylamide) | 77 |
| Tyr—D-Ala—NH—$CH_2CH_2CH_2CH_2$—$C_6H_5$ | (phenylbutylamide) | 13 |
| Tyr—D-Ala—NH—$CH_2CH_2$—$C_8H_6N$ | (tryptamide) | |
| Tyr—D-Ala—NH—$CH(CH_3)CH_2$—$C_6H_5$ | (d-amphetamide) | |
| Tyr—D-Ala—NH—$CH(CH_3)CH_2$—$C_6H_5$ | (l-amphetamide) | |
| Tyr—D-Ala—NH—$C(CH_3)_2CH_2$—$C_6H_5$ | (phentermide) | |
| Tyr—D-Ala—NH—$CH_2CH(CH_3)$—$C_6H_5$ | (beta-methylphenethylamide) | |
| Tyr—D-Phe—$NH_2$ | | 0.1 |
| Tyr—D-Phe—NH—$CH(CH_3)_2$ | (isopropylamide) | |
| Tyr—D-Phe—NH—$CH_2CH(CH_3)_2$ | (isobutylamide) | |
| Tyr—D-Phe—NH—$CH_2CH_2CH_2CH_3$ | (n-butylamide) | |
| Tyr—D-Phe—NH—$CH_2CH_2$—$C_6H_5$ | (phenethylamide) | |
| Tyr—D-Phe—NH—$CH_2CH_2CH_2$—$C_6H_5$ | (phenylpropylamide) | |

| Peptide | Dose (μg/mouse)# | Latency (sec) | Duration (min) |
|---|---|---|---|
| Tyr—D-Ala—Gly—Phe—Met—$NH_2$ | 10 | 6.0 (cutoff) | 150 |
| Tyr—D-Ala—Gly—Phe—Met—$NH_2$ | 1 | 4.6 | 90 |
| Tyr—D-Ala—NH—$CH_2CH_2CH_2$—$C_6H_5$ | 6 | 6.0 (cutoff) | 150 |
| Tyr—D-Ala—NH—$CH_2CH_2CH_2$—$C_6H_5$ | 0.6 | 5.2 | 60 |
| Tyr—D-Ala—NH—$CH_2CH_2CH_2$—$C_6H_5$ | 0.1 | 3.9 | 30 |
| Saline | — | 2.9 | — |

*(Assay on the stimulated guinea pig ileum according to Chipkin, et al.; standard peptide is methionine-enkephalin.)
(In vivo analgesic assay according to Chipkin, et al.; 10 μg of standard = 6 μg of Tyr—D-Ala—phenylpropylamide on a molar basis; latency = time necessary for tail-flick 10 min after injection; duration is return to base latency.)

We claim:

1. A dipeptide derivative having the formula

Tyr-D-Ala-$NR_1$-$(CH_2)_n$-phenyl wherein n is an integer from 1 to 4, and $R_1$ is H or alkyl.

2. The dipeptide derivative of claim 1, wherein Ar is phenyl, R is $(CH_2)_3$, and $R_1$ is H.

3. An analgesic composition comprising an analgetically effective amount of the dipeptide derivative of claim 1, and a pharmaceutically acceptable carrier therefor.

4. A method for effecting analgesia, comprising administering to a mammalian host in need thereof an analgetically effective amount of the composition of claim 3.